(12) United States Patent
Claybourn et al.

(10) Patent No.: US 6,260,997 B1
(45) Date of Patent: Jul. 17, 2001

(54) METHOD AND APPARATUS FOR HIGH SPATIAL RESOLUTION SPECTROSCOPIC MICROSCOPY

(76) Inventors: Michael Claybourn, 17 Middlethorpe Drive, York YO2 2NG; Azzedine Hammiche, Lancaster University Physics Campus, Lancaster LA1 4YB; Hubert Murray Montagu-Pollock, Low Beckfoot, Barbon, Carnforth LA6 2LE; Michael Reading, 11 Snaith Crescent, Loughton, MiltonKeynes MK5 8HU, all of (GB)

(*) Notice: Subject to any disclaimer, the term of this patent is extended or adjusted under 35 U.S.C. 154(b) by 0 days.

(21) Appl. No.: 09/178,349

(22) Filed: Oct. 23, 1998

Related U.S. Application Data
(60) Provisional application No. 60/063,558, filed on Oct. 28, 1997.

(51) Int. Cl.[7] .............................. G01N 25/20; G01J 5/00
(52) U.S. Cl. .............................. 374/45; 374/43; 374/166; 374/124
(58) Field of Search .............................. 374/11, 31, 10, 374/12, 13, 33, 43, 110, 124, 166, 4–7, 45; 250/339.03, 339.04, 339.08, 341.06

(56) References Cited

U.S. PATENT DOCUMENTS

| | | | |
|---|---|---|---|
| Re. 36,529 * | 1/2000 | Lewis et al. | 356/346 |
| 4,956,538 * | 9/1990 | Moslehi | 219/121.6 |
| 5,156,461 * | 10/1992 | Moslehi et al. | 374/128 |
| 5,248,199 * | 9/1993 | Reading | 374/11 |
| 5,378,983 * | 1/1995 | Yagi et al. | 324/158.1 |
| 5,406,377 * | 4/1995 | Dumoulin | 356/346 |
| 5,441,343 * | 8/1995 | Pylkki et al. | 374/137 |
| 5,567,052 * | 10/1996 | Yoshike et al. | 374/124 |
| 5,602,820 * | 2/1997 | Wickramasinghe et al. | 369/126 |
| 5,606,413 * | 2/1997 | Bellus et al. | 356/326 |
| 5,755,511 * | 5/1998 | Peuse et al. | 374/128 |
| 5,923,036 * | 7/1999 | Tague, Jr. et al. | 250/339.07 |
| 6,072,180 * | 6/2000 | Kramer et al. | 250/341.6 |
| 6,095,679 * | 2/1997 | Hammiche et al. | 374/43 |

* cited by examiner

*Primary Examiner*—G. Bradley Bennett
*Assistant Examiner*—Gail Verbitsky
(74) *Attorney, Agent, or Firm*—Shaw Pittman

(57) ABSTRACT

A sample and a scanning probe microscope system are used as the detector for an infrared spectrometer to circumvent the diffraction limit of conventional infrared microscopy, and to provide spectroscopic images with a greatly improved spatial resolution, potentially as low as a few tens of nanometers. The beam from an infrared spectrometer is directed at the sample. The sample is heated to the extent that it absorbs infrared radiation. Thus the resulting temperature rise of an individual region depends upon the particular molecular species present, as well as the range of wavelengths of the infrared beam. These individual temperature differences are detected by a miniature thermal probe. The thermal probe is mounted in a scanning thermal microscope. The scanning thermal microscope is then operated used to produce multiple surface and sub-surface images of the sample, such that the image contrast corresponds to variations in either thermal diffusivity, surface topography or chemical composition.

24 Claims, 7 Drawing Sheets

METHOD AND APPARATUS FOR HIGH SPATIAL RESOLUTION SPECTROSCOPIC MICROSCOPY

The present application claims priority from the filing date of Provisional Patent Application Ser. No. 60/063,558, filed Oct. 28, 1997.

BACKGROUND OF THE INVENTION

1. Field of the Invention

The present invention relates to spectroscopic analysis of individual regions of inhomogeneous samples. The regions to be analyzed are identified, selected and imaged at a high spatial resolution using scanning probe microscopy.

2. Description of the Related Art

Techniques for the photothermal characterization of solids and thin films are widely used, as is described by D. P. Almond and P. M. Patel, "Photothermal Science and Techniques", Chapman and Hall (London and New York, 1996). Recently the ability to add spatial resolution to these techniques has become of technical interest in many fields: one example is the general area of electronic and optical devices. However, most methods commercially available suffer from the limitations imposed by the finite optical wavelengths of the detection systems used. For example, in practice the spatial resolution of the popular but expensive technique of Fourier transform infrared microscopy is seldom better than five to ten micrometers.

Most conventional methods of thermal imaging employ an energy beam that emerges from a small source and spreads out according to the rules of diffraction. The extent of this spreading is normally governed by the wavelength associated with the energy flux. However, if the sample is within the "near-field" region, i.e., significantly less than one wavelength away from the source, then a greatly reduced beam diameter can be achieved. In fact, when the sample is less than one wavelength away from the source, the diameter of the beam is not much larger than the size of the source itself. This principle is applied in Scanning Probe Microscopy. In Scanning Probe Microscopy, a sharp probe is brought into close proximity to the surface of a sample. Some probe/sample interaction takes place. This interaction is monitored as the probe is scanned over the surface. An image contrast is then computer-generated. The image contrast represents variations of some property (e.g., physical, mechanical, chemical) of the sample across the scanned area. One such probe microscope is the Atomic Force Microscope (AFM). In conventional AFM, the height of a probe above the surface being scanned is controlled by a feedback system. The feedback system keeps the force between the probe and the surface of the sample constant. The probe height is monitored, and provides the data that is used to create image contrast which represents the topography of the scanned area.

The use of miniature thermocouple probes and other near-field devices, as part of a scanning probe microscopy system, allows the limitations imposed by diffraction to be overcome, so that near-field scanning photothermal spectroscopy has become recognized as a research technique, as described, for example, by C. C. Williams and H. K. Wickramasinghe in "Photoacoustic and Photothermal Phenomena", P. Hess and J. Petal (eds.), Springer (Heidelberg, 1988). In their device, the probe is a specially made coaxial tip that forms a fine thermocouple junction. This probe provided a spatial resolution of the order of tens of nanometers. The sample is either heated using a laser or the probe, or the sample is heated electrically. The feedback system maintains the probe temperature constant (instead of maintaining the force constant), by varying the probe height as necessary.

J. M. R. Weaver, L. M. Walpita and H. K. Wickramasinghe in Nature, Vol. 342 pp. 783–5 (1989), described experiments that were similar to the Williams and Wickramasinghe experiments, except that the thermocouple junction was formed by contact between a scanning tunnelling microscopy probe (formed from one single electrical conductor) and an electrically conducting sample. They used this setup to perform optical absorption microscopy and spectroscopy with nanometer-scale spatial resolution. Types of image obtained included an electron tunnelling image that was sensitive to variations in surface topography, and a thermal image that was sensitive to variations in optical absorption properties and thermal properties of the sample-substrate system.

In another article, published in Soc. Photo. Instrum. Engrs. Vol. 897, pp. 129–134 (1988), C. C. Williams and H. K. Wickramasinghe used a near-field thermal probe in passive mode to measure photothermally-induced temperature variations in an electron beam-generated grating structure. They suggested that near field thermal and photothermal microscopy would find application in optical absorption spectroscopy at sub-optical lateral resolutions, and for measurement of exothermic and endothermic processes on a small scale.

Further developments in this field are described by E. Oesterschulze, M. Stopka and R. Kassing, Microelectronic Engineering vol. 24 pp. 107–112 (1994), and the field has been reviewed by A. Majumdar, K. Luo, Z. Shi and J. Varesi in Experimental Heat Transfer vol. 9 pp. 83–103 (1996). In "Thermal Imaging Using the Atomic Force Microscope," Appl. Phys. Lett., vol. 62, pp. 2501–3 (1993), Majumdar, et al. describe a technique for thermal imaging that uses a simpler design of thermocouple tip, than that disclosed by Williams and Wickramasinghe. They also implemented standard atomic force microscopy feedback to maintain tip/sample contact. R. B. Dinwiddie, R. J. Pylkki and P. E. West "Thermal Conductivity Contrast Imaging with a Scanning Thermal Microscope," Thermal Conductivity 22, T. W. Tsong (ed.) (1994), describe the use of a probe in the form of a tiny platinum resistance thermometer. U.S. Pat. No. 5,441,343 to Pylkki et al. (the "'343 patent") discloses the thermal sensing probe for use with a scanning probe microscope, in which the contact force of the probe is maintained at a constant level as the probe is scanned across the surface of the sample.

Also relevant is the recently developed technique for localised chemical fingerprinting by means of thermal analysis performed in a scanning thermal microscope. This has been described in U.S. Pat. No. 5,248,199 to Reading et. al (the "'199 patent") and U.S. patent application Ser. No. 08/837,547 to Hammiche et. al (the "'547 application"), both of which are incorporated herein by reference. It has also been described in the following publications: A. Hammiche, H. M. Pollock, M. Song and D. J. Hourston, Measurement Science and Technology 7, 142–150 (1996); A. Hammiche, H. M. Pollock, D. J. Hourston, M. Reading and M. Song, J. Vac. Sci. Technol. B14 (1996) 1486–1491; A. Hammiche, M. Reading, H. M. Pollock, M. Song and D. J. Hourston, Rev. Sci. Instrum. 67,4268 (1996); and H. M. Pollock, A. Hammiche, M. Song, D. J. Hourston and M. Reading, Journal of Adhesion, Vol. 67, pp. 193–205 (1998). That invention relates to the measurement of the thermal properties of materials using a miniaturized resistive thermal probe, and more particularly, to performing localized thermal analysis experiments whereby calorimetric information is obtained from volume of materials of the order of a few cubic microns, whereas in conventional bulk calorimetry data is obtained for volumes of material of a few cubic millimeters. In the course of this work, a means to perform subsurface depth profiling and imaging using thermal waves was also developed.

The other aspect of that invention relates to modulating the temperature of the probe to generate evanescent thermal waves in a material under study to thereby generate sub-surface images. It allowed for application of a modulated temperature differential scanning calorimetry technique, such as described in U.S. Pat. No. 5,224,775 to Reading, et al. (the "'775 patent"), which has been conventionally used to perform bulk thermal analysis experiments of a sample material, to microscopy using two highly miniaturized resistive probes, developed by the Topometrix Corporation and described in the '343 patent, in a differential arrangement. A sample probe, attached to a Scanning Probe Microscope, is positioned at a desired location on the surface within the field of view. Localized calorimetry is then performed at that position by inducing and detecting localized phase transitions. This is achieved by ramping the temperature of the probe by passing an appropriate current through it. To that temperature ramp a small temperature oscillation is superimposed by adding a modulated current into the probe. By scanning over the surface of the sample, contrast can be developed corresponding to particular locations on the sample to create an image of the thermal properties of the sample at the particular locations.

The probe, developed by the Topometrix Corporation, is an elongated loop of Wollaston wire, shaped in the form of a cantilever whose end forms the resistive element. The resistance of that element varies with temperature. Conversely, its temperature can be set by passing a current of appropriate value through it. A mirror is attached across the loop allowing for the contact force of the element on the sample to be held constant, as in conventional atomic force microscopy while the probe is scanned across the surface of the sample.

The probe is used as a highly localised heat source by passing a current through it. Its temperature is set constant and/or time varying. As the probe is brought close to the surface of a sample, heat will flow from the probe to the sample. The amount of heat flowing will vary according to various properties of the sample at the location under the probe. This varying heat flow causes the temperature of the resistive element to change, thereby changing its resistance. A feedback circuit is preferably used to sense the change in the probe resistance (and therefore its temperature) and increase the amount of current flowing through the probe to bring it back to its original resistance value (and therefore its set temperature).

A differential signal is then monitored, either directly or through a lock-in amplifier. The differential signal is used to either (1) to produce localized analysis plots of amplitude and phase data versus temperature that provide calorimetric information at a specific position on the sample, or (2) to construct an image whose contrasts represent variations in thermal conductivity and/or diffusivity across a scanned area. In the second embodiment, the time-varying current through the resistive elements generates thermal waves in the sample. The modulation frequency of the time-varying current is functionally related to the depth below the surface of the sample at which an image of the sample is desired. A sub-surface image is thus generated. The depth of material below the sample surface that is contributing to the image can be controlled by suitably choosing the temperature modulation frequency. As described in Almond, et al., "Photothermal Science and Techniques," page 15, Chapman and Hall (London 1996), which is hereby incorporated by reference in its entirety, the penetration depth is proportional to the square root of the thermal diffusivity of the sample divided by the frequency of the applied temperature wave.

It would be advantageous to be able to extend such chemical fingerprinting techniques to give true chemical analysis. Previous work on optical absorption spectroscopy combined with near-field microscopy has either been limited to the study of electrically conductive samples or has been restricted to the use of individual wavelengths of the incident light. Moreover, no reliable way has been described of deconvoluting spatial variations in thermal properties from the local variations in infrared absorption which are the key to localised spectroscopic analysis. Thus, so far there has been no report of such techniques having been applied to chemical analysis by means of spectroscopy at high spatial resolution, and this is the subject to which the present invention relates. Each publication, patent and patent application referred to herein is hereby incorporated by reference in its entirety herein.

SUMMARY OF THE INVENTION

In the present invention, high spatial resolution spectroscopic images are obtained by using a sample and a scanning probe microscope system as the detector for an infrared spectrometer. This circumvents the diffraction limit of conventional infrared microscopy, and thus provides spectroscopic images with a greatly improved spatial resolution (potentially as low as a few tens of nanometers).

The beam from an infrared spectrometer is directed at the sample. The sample is heated to the extent that it absorbs infrared radiation, i.e., the extent of the resulting temperature rise of an individual region depends upon the particular molecular species present (as well as the range of wavelengths of the infrared beam). These individual temperature differences are detected and measured by a miniature thermal probe. The thermal probe is mounted in a scanning thermal microscope. The scanning thermal microscope is then operated to produce multiple surface and sub-surface images of the sample, such that the image contrast corresponds to variations in thermal diffusivity, surface topography, chemical composition or other property of the surface material.

OBJECTS OF THE INVENTION

An object of the present invention is to obtain scanning thermal microscope images of a sample, in which the image contrast is determined by variation in the amount of heat absorbed by infrared (or other electromagnetic) radiation to which the sample is exposed, i.e., by variation in chemical composition.

Another object of the present invention is to analyze individual regions of a sample spectroscopically. The images can be selected from scanning probe images obtained with the use of the same thermal probe or by other methods.

Another object of the present invention is to deconvolute spatial variations in thermal properties from the local temperature variations due to infrared absorption which are the key to localized spectroscopic analysis.

Another object of the present invention is to use a miniature temperature-sensing probe to measure the rate at which heat is absorbed by a sample exposed to electromagnetic radiation.

Another object of the present invention is to perform dispersive infrared microscopy at a high spatial resolution that is not diffraction-limited, using radiation whose wavelength has been restricted to a chosen band within the infrared region of the electromagnetic spectrum.

Another object of the present invention is to perform Fourier transform infrared microscopy at a high spatial resolution that is not diffraction-limited, using unfiltered broad-band radiation.

Another object of the present invention is to provide a resistive thermal probe which serves as a point source of heat (in addition to sensing temperature and performing the functions listed in the objects above), such that it can produce the high-frequency temperature modulation that is needed for the user to choose the volume of material being spectroscopically analyzed at each individual location selected.

DETAILED DESCRIPTION OF THE INVENTION

Apparatus

Figure 1A:
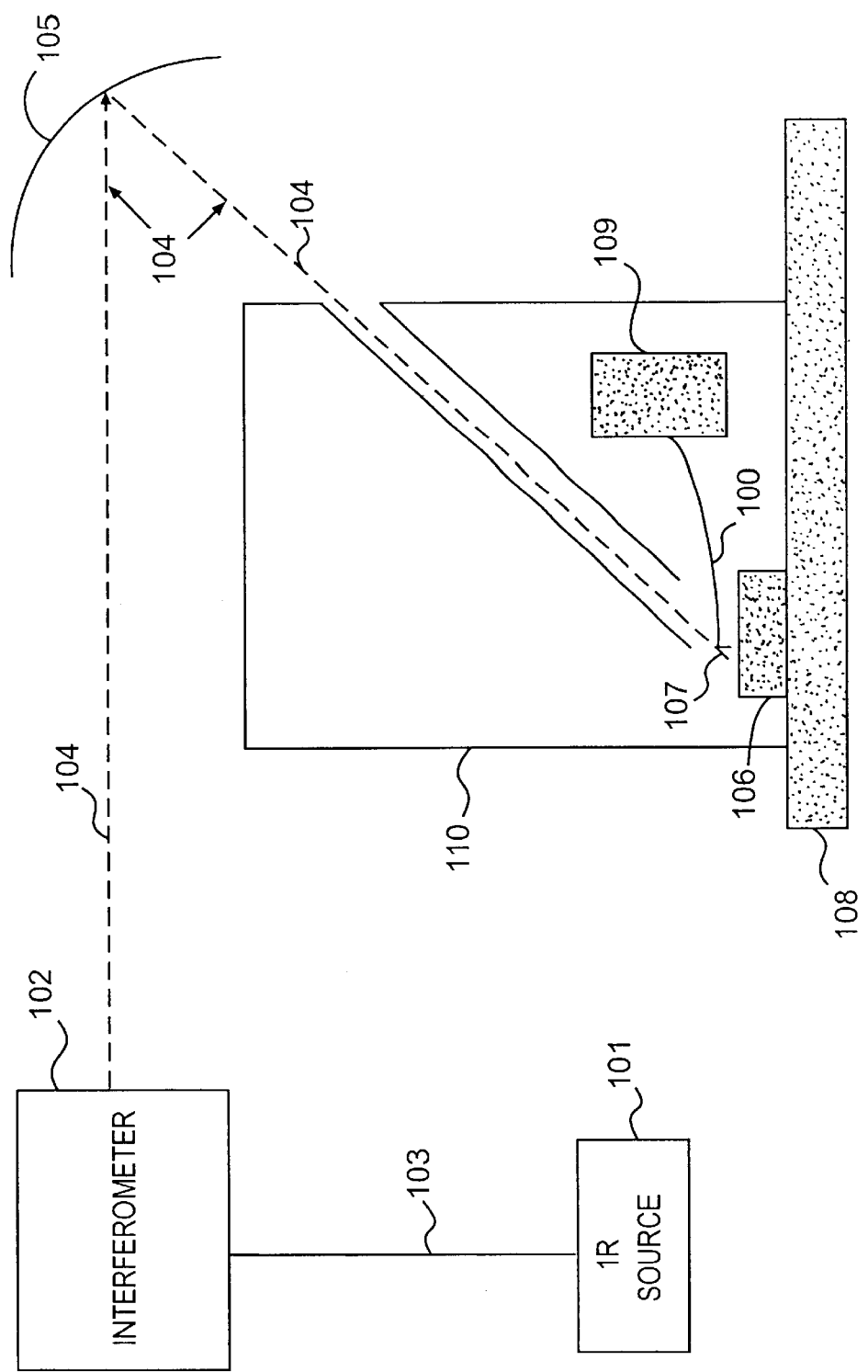
FIG. 1a is a schematic diagram of the overall layout of the invention, using a Fourier transform infrared spectrometer.

As shown in FIG. 1a, the first embodiment of the present invention uses the IR source 101 and interferometer 102 in a Fourier Transform Infrared (FTIR) spectrometer. Interferometer 102 could be a Michelson interferometer or any other type of interferometer suitable for FTIR spectrometry. Unmodulated beam 103 is modulated by interferometer 102. The IR beam emerges from interferometer 102 as modulated beam 104. Beam 104 is directed by mirror 105 onto the surface of sample 106 mounted on stage 108 in scanning thermal microscope 110. The tip 107 of thermal probe 100 is positioned on sample 106 at the same position that IR beam 104 is incident on the sample. Module 109 controls and measures the temperature and current of the thermal probe, and controls the position of the thermal probe as described in the '547 application. Probe 100 can be either a passive probe or an active probe. In both cases, a second probe of identical type can be used as a reference probe, such that the measurement performed is differential in nature.

The passive type of probe is typically a miniature thermometer only, such as a thermocouple probe as described by Wickramasinghe, Majumdar or Weaver, or a resistive Wollaston-type probe, of the type described in the '547 application or the '343 patent, used in the passive mode.

The active type of probe is used as both a thermometer and as a heater. It uses a Wollaston-type of resistive probe, of the type described in the '547 application or the '343 patent.

Scanning thermal probe microscope 110 is described, for example, in Majumdar, the '199 patent and the '547 application.

Figure 1B:
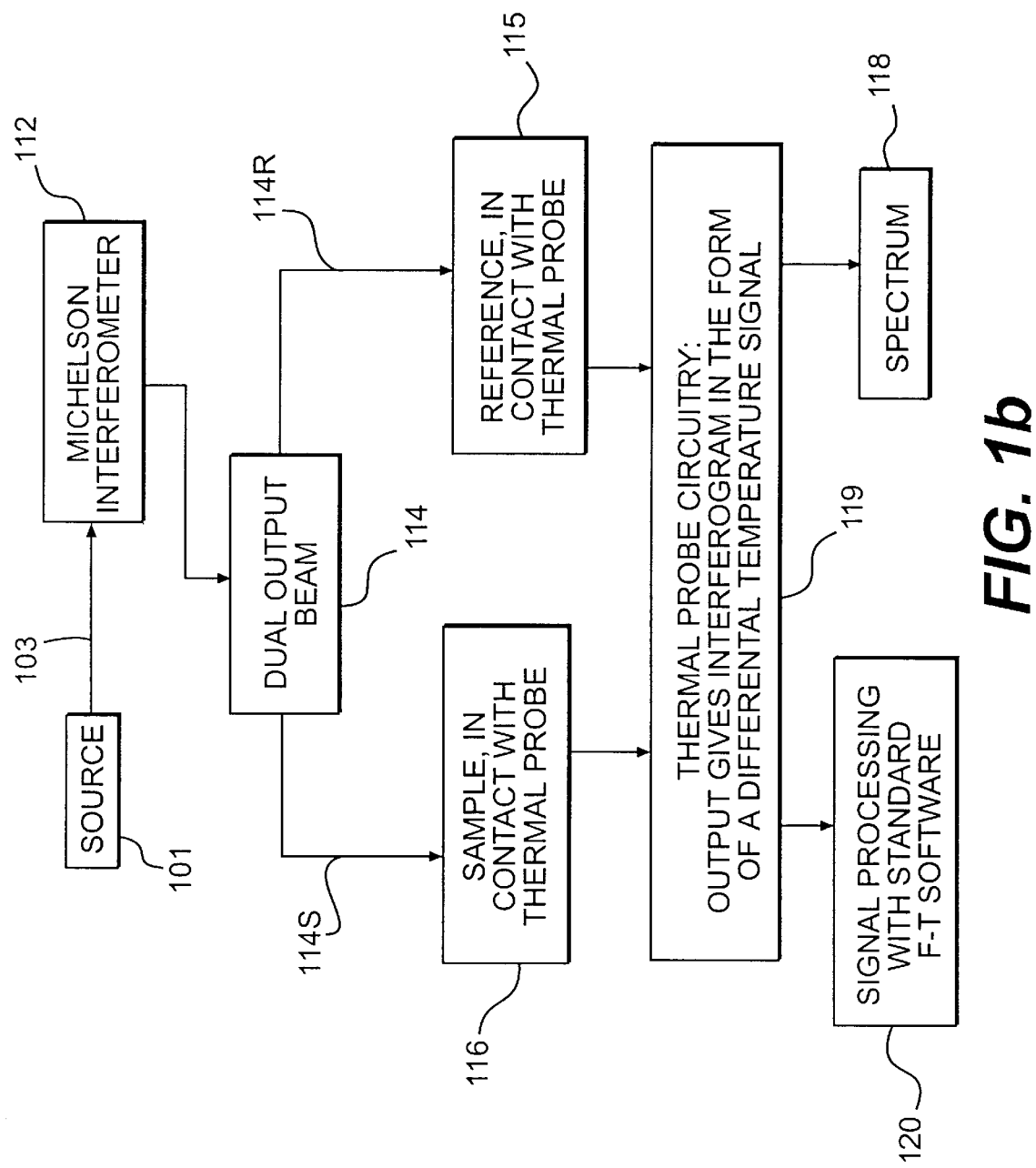
FIG. 1b is a schematic block diagram of the invention using a dual output beam Fourier transform spectrometer.

FIG. 1b is a schematic block diagram of the first embodiment of the present invention, implemented using a dual-beam interferometer. In this case, the output of interferometer 112 is a dual output beam 114. Beam 114S is directed at the sample in contact with the thermal probe. Beam 114R is directed at a reference, which is also in contact with a thermal probe. Module 119 contains the circuitry and other hardware and software for controlling and measuring the temperature of the thermal probes. The thermal probes are connected differentially, such that the output signal is a differential signal representing the differential temperature of the sample probe with respect to the reference probe.

Figure 1C:
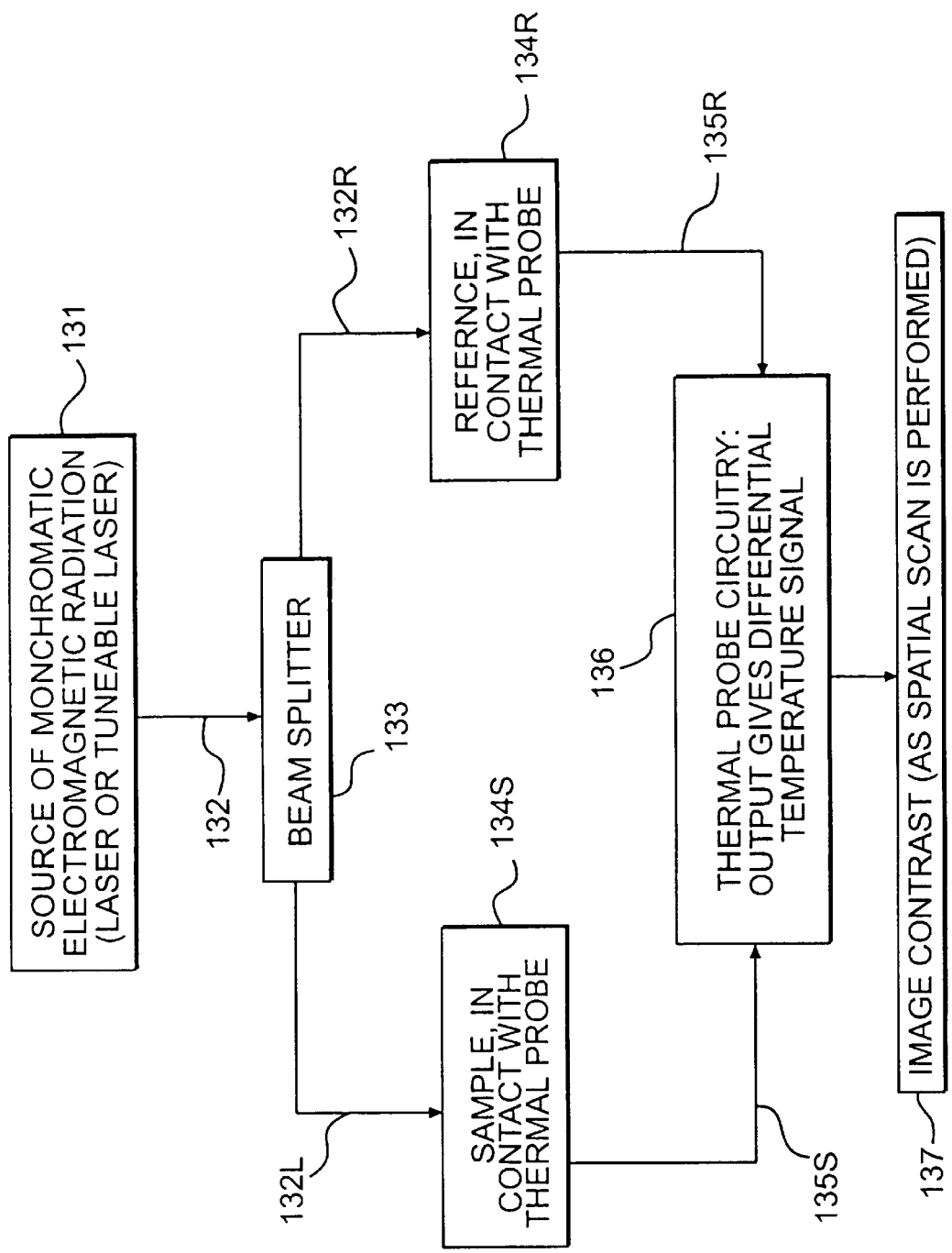
FIG. 1c is a schematic block diagram of the present invention, using a source of monochromatic radiation.

As shown in FIG. 1c, the source 131 of electromagnetic radiation could also be a laser or a tunable laser. Beam 132 is preferably modulated, i.e., source 131 is preferably a source of modulated electromagnetic radiation. Beam 132 is then split by beam splitter 133 into sample and reference beams 132S and 132R, respectively. As in the FTIR embodiment, the sample beam is incident at the surface of the sample 134S at the same position as the position of the sample thermal probe. The reference beam 132R is incident on the surface of a reference at the same position as the position of the reference thermal probe. A sample electrical signal and a reference electrical signal are then input to the thermal probe module 136, which then outputs a differential temperature signal. Alternatively, the sample and reference thermal probes are connected electrically so as to produce a differential electrical signal representing the differential signal from the sample with respect to the reference directly. In either case, the differential signal is used to provide image contrast, as the sample is scanned relative to the thermal probes (or as the thermal probes are scanned relative to the sample).

The apparatus of FIG. 1c could also be modified to operate without a reference beam. In this case, beam splitter 133 is not used, and a single beam is directed to a single thermal probe on the sample, to record sample data, and a second measurement is carried out with a reference to record reference data. The ratio of the sample data to the reference data (or alternatively the sample data minus the reference data), is then calculated at each position of the sample with respect to the thermal probe to provide the image as a spatial scan of the sample with respect to the reference is performed.

Figure 1D:
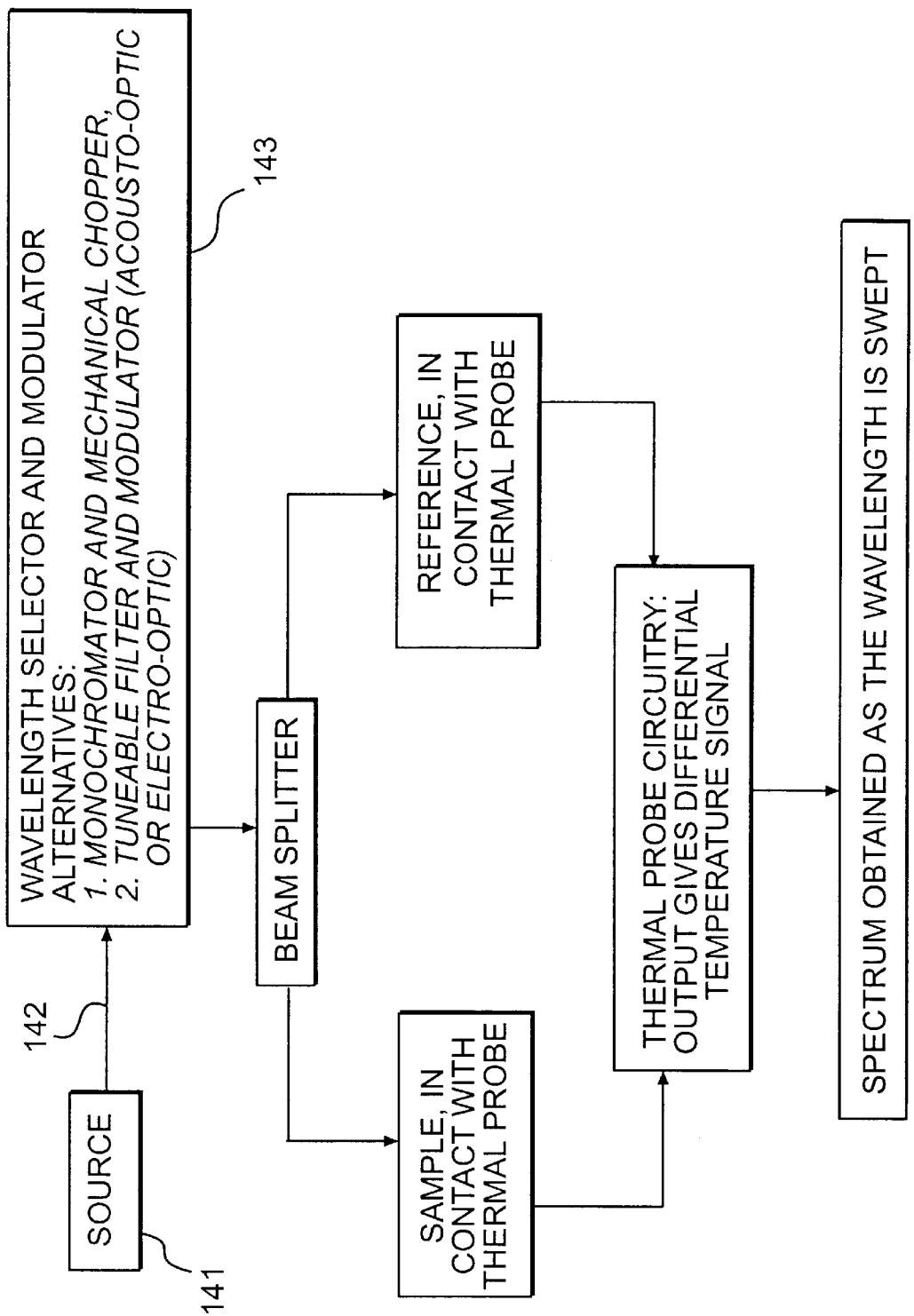
FIG. 1d is a schematic block diagram of the present invention, using a spectrometer to the electromagnetic radiation.

FIG. 1d is a schematic block diagram of the use of a spectroscopic apparatus with the present invention. The apparatus comprises source 141 which directs beam 142 at wavelength selector and modulator 143 (such as a monochromator and a chopper, a tuneable filter with an acousto-optic or electro-optic modulator, a liquid crystal tuneable filter or a holographic filter).

Mode of Operation

In one preferred mode of practicing the present invention, the image contrast is obtained from the variation in the amount of heat absorbed from the infrared or other electromagnetic radiation to which the sample is exposed, which is indicative of variations in the chemical composition of the surface. The scanning thermal microscope is positioned over the sample and the radiation is focussed onto the region of the sample that is to be imaged. The variation in temperature from one point to another on the sample surface is determined by local variations in absorption coefficient, thermal conductivity, and thermal diffusivity. The intensity of the incident radiation may be modulated by means of a mechanical chopper or by one of the other types of modulator listed above. Either type of passive thermal probe is then brought into contact with the sample and the contact force between probe and sample is set by the force feedback control that is standard procedure in atomic force microscopy. The thermal probe and the IR beam are then scanned with respect to the sample, and the image contrast is determined by the difference between the signal from the sample probe, acting as a thermometer, and (b) the signal from the reference probe. In this case, all the raw data takes the form of differential measurements. This apparatus can also be used to measure the rate at which heat is absorbed by a sample exposed to electromagnetic radiation.

Figure 2:
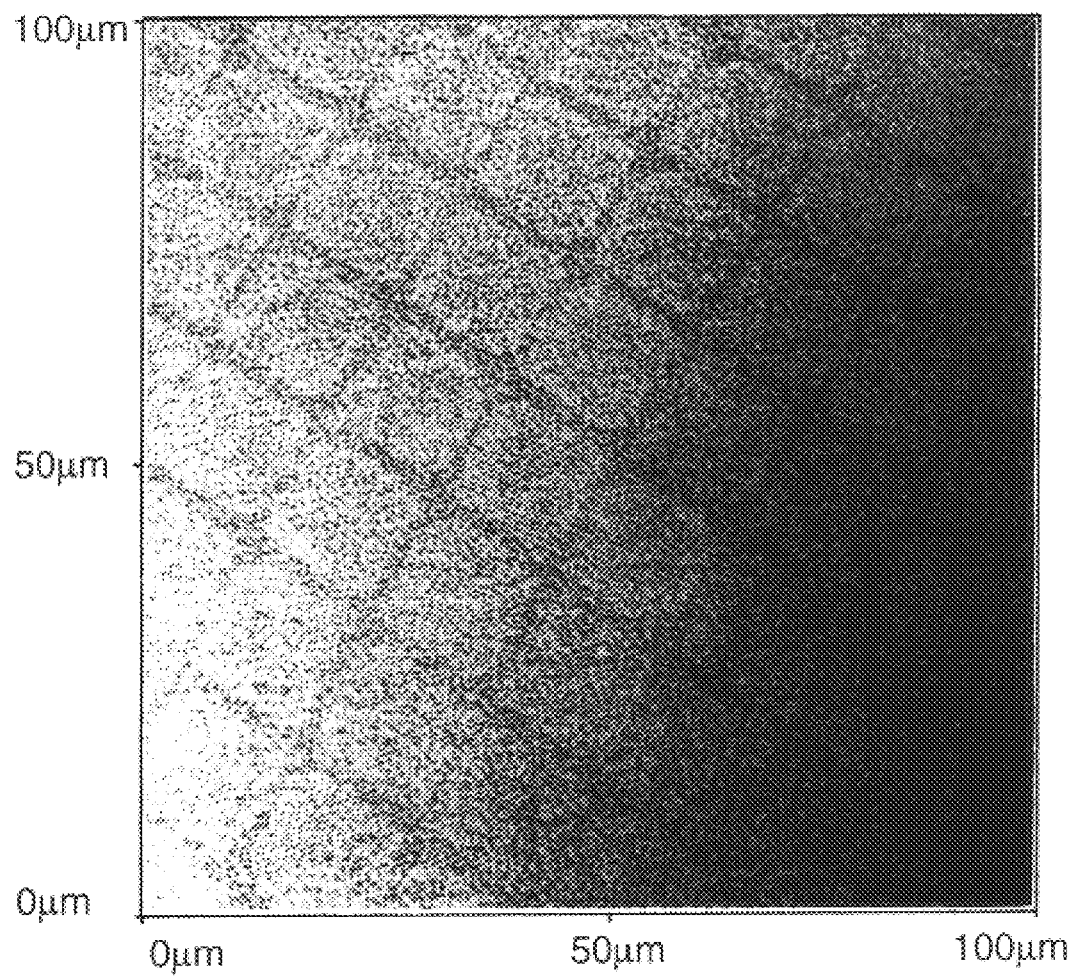
FIG. 2 is a photothermal image of a silicon/silicon dioxide grid, irradiated with visible light from a helium-neon laser.

An example of such image contrast is shown in FIG. 2. FIG. 2 is a photothermal image of a silicon/silicon dioxide grid, irradiated with visible light from a helium-neon laser. The contrast in the image results from the differential heating of the two materials to two different temperatures, due to the differential absorption of the He—Ne light by the two different materials, as revealed by a resistive thermal probe used in passive mode.

The present invention can also be used for Fourier transform infrared microscopy at a high spatial resolution that is not diffraction-limited. The FTIR uses unfiltered broad-band radiation. The scanning thermal microscope is positioned over the region of the sample to be analyzed, and the probe is brought into contact under force feedback as above. Infrared light from a Fourier transform infrared spectrometer is focussed onto the point of contact between probe and sample, using the apparatus for focussing and directing the beam shown in FIG. 1a. The light is modulated by the interferometer. It causes localised heating of the sample due to absorption by chemical functional groups. The thermal wave generated is directly detected by the probe, used in passive mode. The thermal time constant of the probe is sufficiently short such that the probe responds to the modulation produced by the interferometer. This time constant depends upon how much of the probe itself, as distinct from the sample, is heated directly by the infrared beam. The underlying science is similar to that of infrared photoacoustic spectroscopy. The thermal interferogram captured from the output of the signal and reference probes, obtained in differential form, is stored on the infrared workstation. The interferograms are then transformed as in standard Fourier transform infrared spectroscopy, to provide a frequency spectrum.

The small size of the thermal probe, which is chosen to provide a short thermal time constant and high spatial resolution, may in some cases result in a relatively low signal to noise ratio as compared with standard infrared spectroscopy. In such cases, averaging of repeated data scans will be necessary. If each individual scan is so weak that the interferogram centerburst is below the noise level, then the dynamic alignment principle generally used in FTIR data averaging will be useless. However even in this situation, successive scans may still be averaged provided that the FTIR instrument is of a type that aligns the scans in relation to an absolute reference that does not depend upon identification of the center-burst feature of any individual scan.

Figure 3:
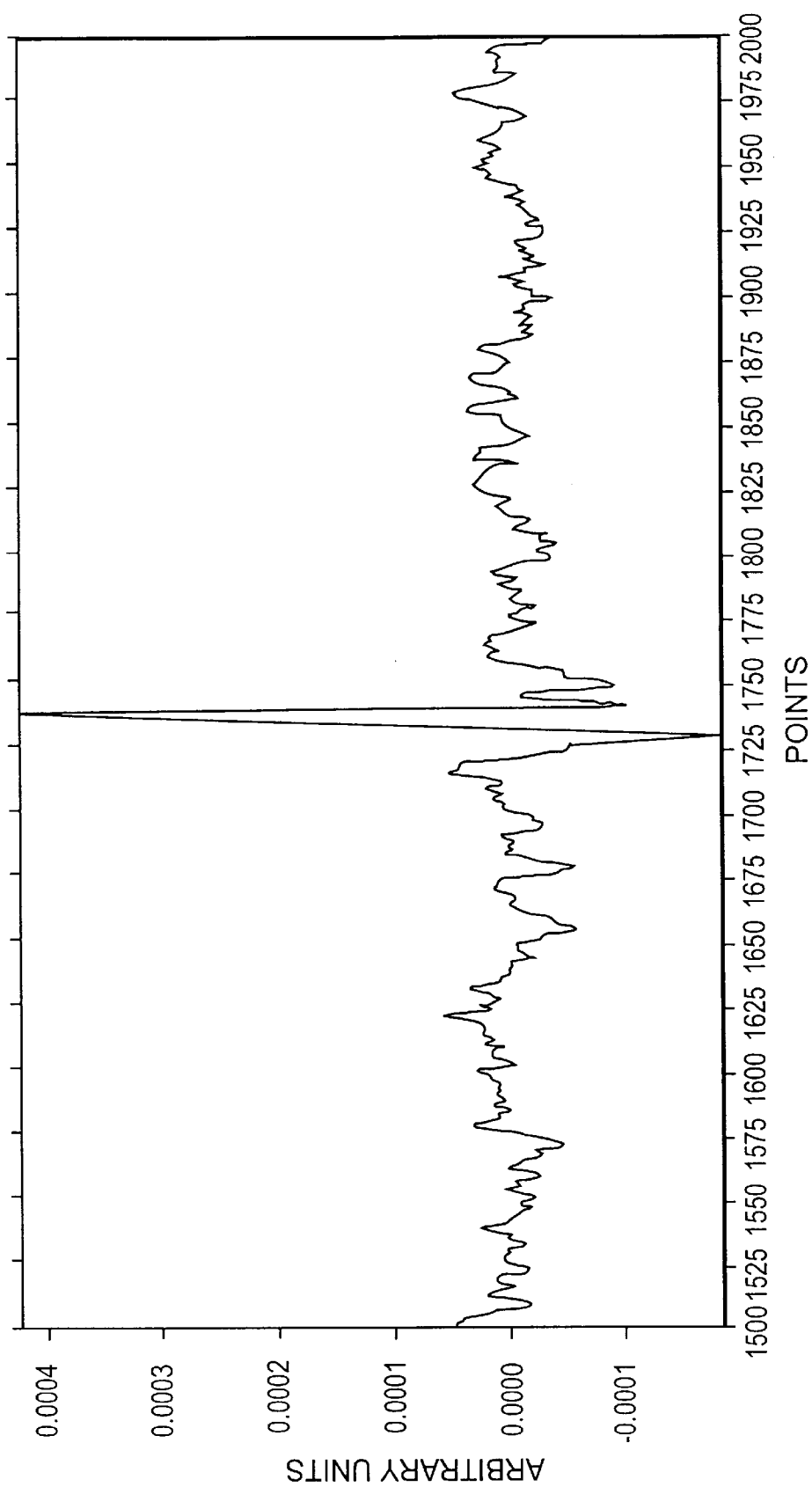
FIG. 3 is an interferogram obtained using the system shown in FIG. 1a, of a polystyrene sample at resolution 16 $cm^{-1}$ using a mirror velocity 0.051 cm/sec.
Figure 4:
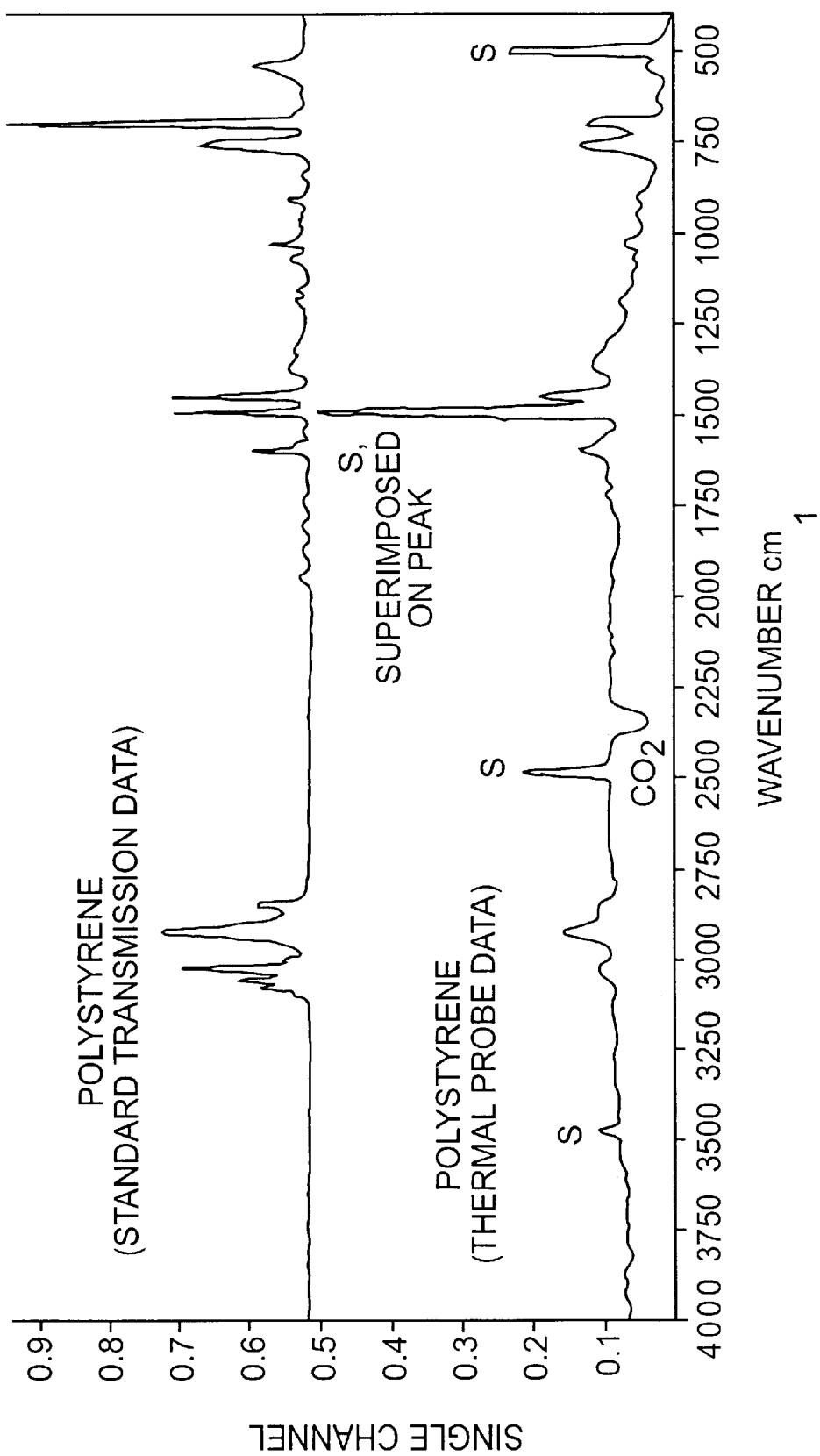
FIG. 4 is a comparison of a polystyrene spectrum obtained using conventional FTIR (upper trace) to a spectrum obtained by transforming the data of FIG. 3 (lower trace).

An example of an interferogram obtained by this method is shown in FIG. 3, and the resulting processed spectrum is shown as the lower trace in FIG. 4. The peaks denoted by S arise from line frequency noise. The remaining peaks are consistent with those shown in the spectrum obtained from a standard FTIR scan, which is shown in the upper trace in FIG. 4.

The present invention may be used to perform spectroscopic analyses on individual regions of a sample, selected from scanning probe images obtained with the use of the same thermal probe or otherwise. The sample is imaged by means of the scanning probe microscope, coupled to the Fourier transform infrared spectrometer as described above. The probe is used in the active mode, so that in addition to the topographic image, both non-modulated and modulated thermal images will be obtained allowing different component phases (chemical or morphological) to be distinguished. The probe is then repositioned under computer control as described in '547 application, to a point of interest for the infrared measurement which is performed as in (3) above. In this case, the spatial resolution of the image is determined by the probe tip dimension, the probe response time constant, the thermal diffusion length in the sample, the optical absorption depth of the sample, and the interferometer's modulation frequency.

In the embodiment of the present invention shown in FIG. 1d, the wavelength of the incident electromagnetic radiation is restricted to a chosen band within the infrared region of the electromagnetic spectrum using a monochromator or a tuneable filter. The data is not Fourier transformed to obtain a spectrum, but otherwise the operation of the instrument is similar to that described above for the FTIR embodiment of the invention. This is confirmed by calculations based upon well-established principles of photoacoustic spectroscopy.

The temperature-sensitivity of the types of thermal probe use in scanning thermal probes is better than 10 mK. Calculated values of temperature rise, under the experimental conditions of the present invention, exceed this value in a number of different cases of interest, as summarized in Appendix A. These calculations take into account the values of beam flux obtainable in practice, and apply to samples whose thermal and absorptive properties are typical of a number of polymer materials. They consider cases in which the near-surface region of the sample is (i) thermally thick and optically opaque, (ii) thermally thick, and either optically transparent or optically opaque but photothermally transparent, (iii) optically transparent and thermally thin.

Another mode of practicing the present invention is to provide a resistive thermal probe which serves as a point source of heat in addition to sensing temperature and performing the functions listed in the objects above. This will produce the high-frequency temperature modulation that is needed for the user (a) to choose the volume of material being spectroscopically analyzed at each individual location selected, and (b) to use modulated thermal imaging for determination of local variations in thermal diffusivity. This enables spatial variations in thermal properties to be deconvoluted from the local temperature variations in infrared absorption which are the key to localised spectroscopic analysis.

It should also be noted that, as described in the '547 application and other publications, the depth below the surface contributing to image contrast in scanning thermal microscopy may be controlled through the use of temperature modulation. The depth is proportional to the square root of the ratio of thermal diffusivity to modulation frequency.

The present invention can also be used with the modulated thermal analysis techniques disclosed in the '547 application to identify chemical species or phases at or near the surfaces of materials.

The present invention can be used in either a dual beam mode—as shown in FIGS. 1b–1d—or in a single beam mode. When used with only a single beam, a reference spectrum is stored (taken either before or after the sample spectrum), and the sample spectrum is ratio'd against the reference spectrum, or the reference spectrum is subtracted from the sample spectrum. A single reference spectrum may be used with a number of sample spectra, or, for increased reproducibility, the sample and reference spectra may be obtained sequentially such that one reference spectrum is obtained immediately after (or immediately before) each sample spectrum.

APPENDIX A (see D. W. van Krevelen, *Properties of Polymers*, Elsevier 1990)

The calculations below assumes the material has the values of parameters of polyethylene.

Notation:

Thermal conductivity $k=0.15$ Wm$^{-1}$ °KE$^{-1}$

Density×heat capacity $\rho C_p = 10^6$ Jm$^{-3}$ °K$^{-1}$

Diffusivity $D=k/(\rho C_p) = 1.6 \times 10^{-7}$

Thermal diffusion length $\mu$ is given by $\mu^2 = D/(\pi v)$, where $v$ is frequency.

Optical absorption length for IR within a typical absorption band:

$l_\beta = 2.5$ $\mu$m (absorption coefficient=$4 \times 10^5$ m$^{-1}$, but can vary two orders of magnitude from one "edge" to another. With visible light, $l_\beta = 10^{-4}$.

IR bandwidth ($\Delta\lambda$) chosen: 200 nm.

Thickness of the near-surface layer of interest: $z_s$=either film thickness, or $=\mu$, see above ("bulk" samples).

Illuminated area of sample: 1 mm$^2$

Power of source: 100 mW

Power per nm of the absorption band: $0.7 \times 10^{-6}$ (the implied ratio $R=1.4 \times 10^4$)

Flux, $I_0 = 1 \times 10^5$ Wm$^{-2}$

Flux per nm of the absorption hand. $I_1 = I_0/R = 7$

Flux per band 200 nm wide: $I_2 = I_1 \times 200 = 1400$ Wm$^{-2}$

Simple theory used, and quantitative examples of temperature rise expected. These are order of magnitude estimates. Some small numerical factors have been omitted from the formulae:

1. Thermally Thick and Optically Opaque Sample (Rosencwaig's case 2b, $\mu<Z_s$, $\mu>l_\beta$, $l_\beta<Z_s$):

$$T = \frac{I_2 \mu}{k}$$

| Example: Thick sample: | v (Hz) | $\mu$ ($\mu$m) | $\Delta T$ (mK) |
|---|---|---|---|
| | 100 | 22 | 20 |
| | 1000 | 7 | 6 | varying as 1/(sq. root of frequency).

2. Thermally thick ($\mu<Z_s$), and either optically transparent (Rosencwaig's case 1c, $l_\beta>Z_s$), or optically opaque but photothermally transparent (Rosencwaig's case 2c, $\mu<l_\beta$):

$$T = \frac{I_2}{l_\beta (\rho C)_p} \times 1/v$$

| Example: | v | $\mu$ ($\mu$m) | $\Delta T$ (mK) |
|---|---|---|---|
| Bulk sample | 30 kHz | 1.2 | 20 |
| $\leq 2$ $\mu$m film | 30 kHz | 1.2 | 20 | varying as 1/(frequency).

3. Optically Transparent and Thermally Thin (Rosenewaig's cases 1a and 1b, $l_\beta>Z_s$, $\mu>Z_s$):

$$T = I_2(z_s/l_\beta)(\mu/k)_{substrate}$$

$$= I_2(z_s/l_\beta) \cdot 1/\sqrt{(\rho\ C_p\ k)_{substrate}} \times 1/\sqrt{v}$$

| Example: 100-nm film | v (Hz) | $\Delta T$ (mK) |
|---|---|---|
| | 100 | 15 |
| | 1000 | 5 | varying as 1/(sq. root of frequency).

What is claimed is:

1. A spectroscopic imaging apparatus comprising:
   (a) a beam of electromagnetic radiation directed at a position on a sample surface;
   (b) a thermal probe positioned at a location at which the beam of electromagnetic radiation is incident at the position on the sample surface, within a near-field of the surface;
   (c) means for controlling the temperature and position of the thermal probe;
   (d) means for scanning the sample relative to the position of the thermal probe and the incident electromagnetic beam;
   (e) means for obtaining spectroscopic data at a plurality of positions on the sample as the sample is scanned and as the temperature of the thermal probe is controlled; and
   (f) means for computing spectroscopic images of the sample from the plurality of spectroscopic data.

2. The apparatus of claim 1, wherein the apparatus comprises an interferometer that provides the beam of electromagnetic radiation, and wherein the means for obtaining spectroscopic data comprises means for Fourier transforming interferograms.

3. The apparatus of claim 1, wherein the apparatus comprises a monochromator and a modulator.

4. The apparatus of claim 3, wherein the modulator is a mechanical chopper.

5. The apparatus of claim 1, wherein the source of electromagnetic radiation is a laser.

6. The apparatus of claim 1, wherein the thermal probe is a passive thermal probe.

7. The apparatus of claim 1, wherein the thermal probe is an active thermal probe.

8. The apparatus of claim 1, wherein the thermal probe is a resistive probe which serves as a point source of heat, and wherein the thermal probe is used to modulate the temperature at a position on the sample at a high frequency.

9. The apparatus of claim 1, further comprising a reference thermal probe.

10. The apparatus of claim 9, wherein the thermal probes are connected differentially, such that the output signal from the thermal probes is a differential signal.

11. A method for obtaining an image of a surface of a sample comprising:
(a) placing the sample in a scanning thermal microscope;
(b) positioning a thermal probe having a tip on the surface of the sample;
(c) directing a beam of electromagnetic radiation at the surface of the sample at the position of the thermal probe on the surface of the sample, the probe positioned to be within a near-field of the surface of the sample;
(d) controlling and measuring the temperature of the tip of the thermal probe to obtain a measure of the extent of the temperature rise at the surface of the sample due to absorption of the electromagnetic radiation at the position of the thermal probe on the sample;
(e) recording the measure of the extent of the temperature rise at the surface of the sample;
(f) scanning the thermal probe and the electromagnetic beam relative to the sample surface, and recording the measure of the extent of the temperature rise as a function of the position of the thermal probe; and
(g) calculating at least one thermal image of the surface of the sample, wherein the thermal image has contrast corresponding to variations in properties of the surface of the sample.

12. The method of claim 11, further comprising positioning a reference thermal probe on the surface of the sample, wherein the measure of the extent of the temperature rise is recorded as a measure of a differential temperature rise of the thermal probe with respect to the reference thermal probe.

13. The method of claim 11, wherein the electromagnetic beam is provided by an interferometer.

14. The method of claim 11, wherein the electromagnetic beam is provided by a monochromator.

15. The method of claim 11, wherein the electromagnetic beam is provided by a laser.

16. The method of claim 11, wherein the electromagnetic beam is modulated.

17. The method of claim 11, wherein only a single electromagnetic beam is used, and wherein the extent of the temperature rise for a sample scan is measured with respect to the extent of the temperature rise for a reference scan taken sequentially.

18. A method for obtaining spectroscopic thermal images of a surface of a sample comprising:
(a) placing a sample in a scanning thermal microscope;
(b) directing a beam of electromagnetic radiation from an interferometer at a surface of the sample, wherein said interferometer has a scanning mirror;
(c) positioning a tip of a thermal probe on the surface of the sample where the beam is incident on the surface of the sample, within a near-field of the surface of the sample;
(d) controlling and measuring the temperature of the tip of the thermal probe to obtain a measure of the extent of the temperature rise at the surface of the sample due to absorption of the electromagnetic radiation at the position of the thermal probe on the sample as a function of the position of the scanning mirror;
(e) recording the measure of the extent of the temperature rise at the surface of the sample;
(f) scanning the thermal probe and the electromagnetic beam relative to the sample surface, and recording interferograms of the extent of the temperature rise as a function of the position of the scanning mirror at a plurality of positions on the surface of the sample;
(g) transforming the interferograms into spectra;
(h) calculating spectroscopic thermal images of the surface of the sample, wherein the thermal images have contrast due to variations in absorption of electromagnetic radiation by the surface of the sample.

19. The method of claim 18, further comprising obtaining reference spectra, wherein the step of calculating spectroscopic thermal images comprises calculating the ratio of the spectra obtained in step (g) to the reference spectra.

20. The method of claim 18, comprising detecting the absorption of the electromagnetic radiation using a thermal probe in the passive mode.

21. The method of claim 18, comprising detecting the absorption of the electromagnetic radiation using a thermal probe in the active mode.

22. The method of claim 18, further comprising modulating the temperature of the tip of the thermal probe such that the temperature of the surface of the sample is correspondingly modulated.

23. The method of claim 22, further comprising distinguishing different component phases on the surface of the sample.

24. The method of claim 22, further comprising selecting the volume of material by selecting the frequency of the temperature modulation.

* * * * *